(12) United States Patent
Evans

(10) Patent No.: US 7,981,682 B2
(45) Date of Patent: *Jul. 19, 2011

(54) HIGH RESOLUTION FLOW CYTOMETER

(75) Inventor: Kenneth M. Evans, College Station, TX (US)

(73) Assignee: XY, LLC, Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/927,620

(22) Filed: Nov. 19, 2010

(65) Prior Publication Data

US 2011/0091963 A1   Apr. 21, 2011

Related U.S. Application Data

(62) Division of application No. 10/524,793, filed as application No. PCT/US03/25812 on Aug. 15, 2003, now Pat. No. 7,855,078.

(60) Provisional application No. 60/404,279, filed on Aug. 15, 2002.

(51) Int. Cl.
*G01N 15/00* (2006.01)
*G01N 19/00* (2006.01)

(52) U.S. Cl. ....... 436/63; 73/865.5; 73/865.8; 324/71.4; 356/440; 356/441; 356/442; 436/10; 435/287.1; 422/73

(58) Field of Classification Search ............. 436/63, 436/10; 73/86.5, 865.5, 865.8; 324/71.4; 356/440–442; 422/73; 435/287.1
See application file for complete search history.

(56) References Cited

U.S. PATENT DOCUMENTS 6,230,982 B1 * 5/2001 Newton ................. 239/10
6,604,435 B2 * 8/2003 Buchanan et al. ......... 73/865.5

OTHER PUBLICATIONS

U.S. Appl. No. 10/524,793, filed Oct. 20, 2005.
International Patent Cooperation Treaty Application PCT/US2003/025812, filed Aug. 15, 2003.
U.S. Appl. No. 60/404,279, filed Aug. 15, 2002.

* cited by examiner

*Primary Examiner* — Krishnan S Menon
*Assistant Examiner* — Rebecca Fritchman
(74) *Attorney, Agent, or Firm* — Craig R. Miles; CR Miles, P.C.

(57) ABSTRACT

High resolution particle differentiation process and separation system that provides enhanced resolution of particles based upon selected particle characteristics. In particular, the system may include an enhanced resolution flow cytometer. In an embodiment, the invention can include at least one fluid source conduit (24) that introduces 0 fluid source stream (24) into an enhanced resolution nozzle (25) at an angle that enhances particle resolution by the cell sensing system (13).

15 Claims, 11 Drawing Sheets

Fig 2
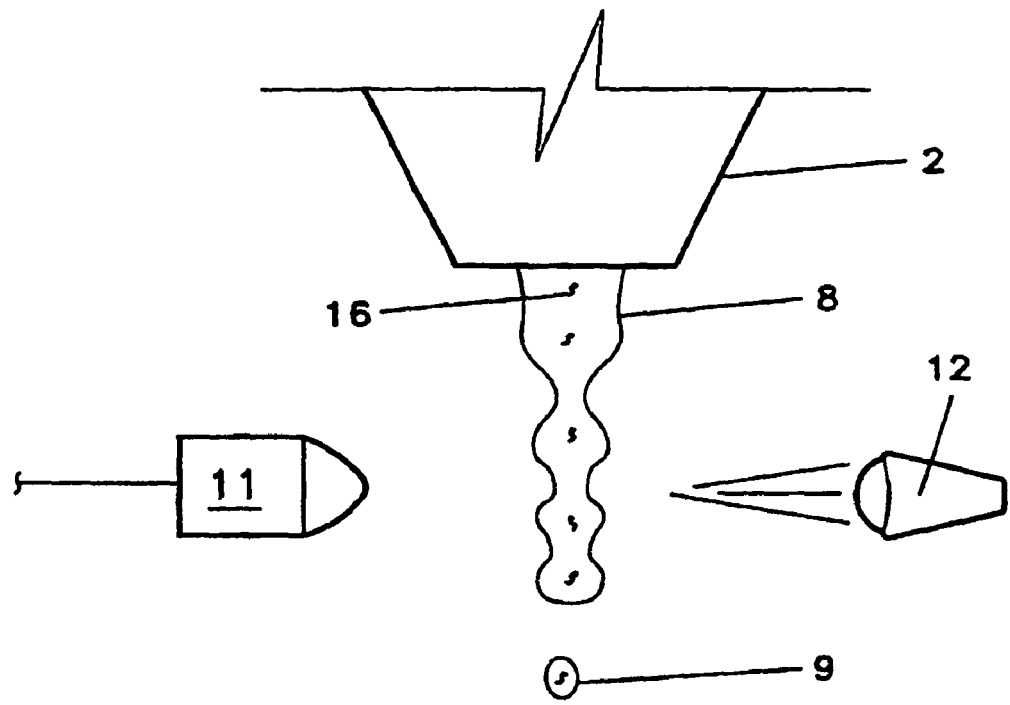
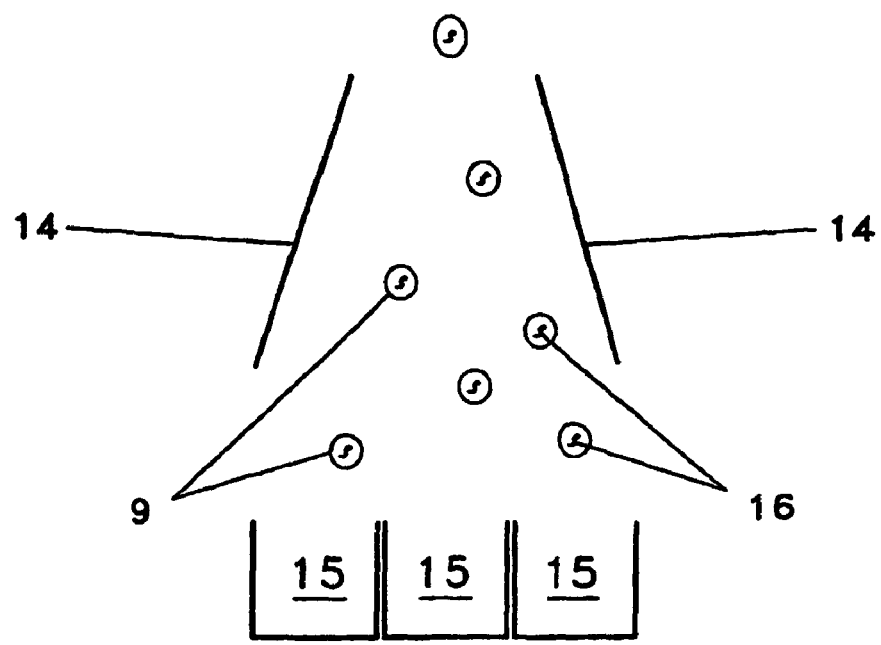

Fig 4
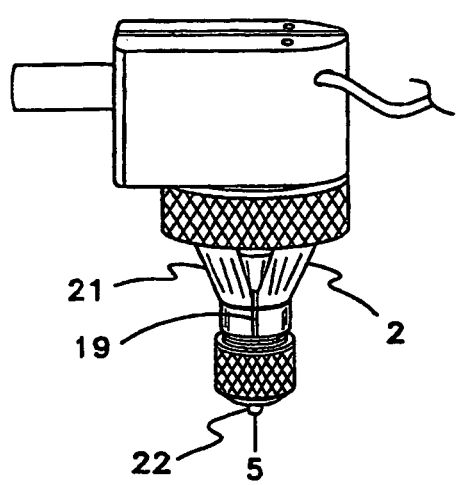
Fig. 4A
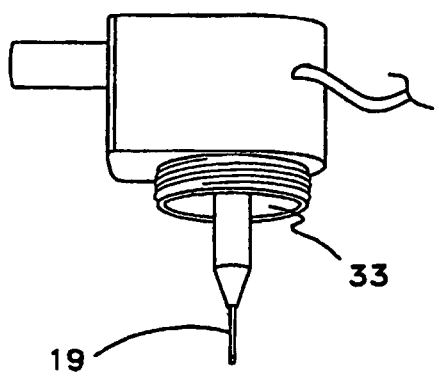
Fig. 4B
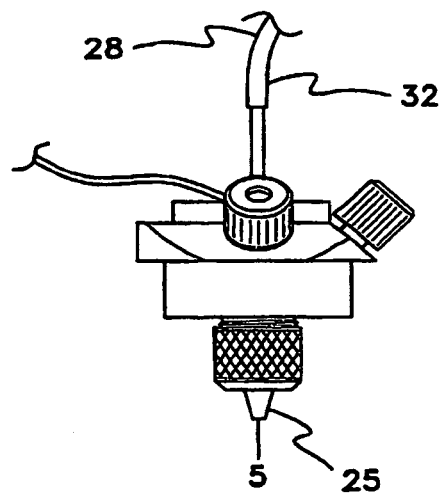
Fig. 4C
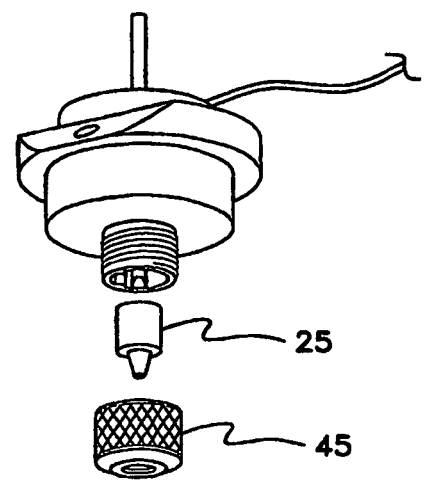
Fig. 4D

Fig 5
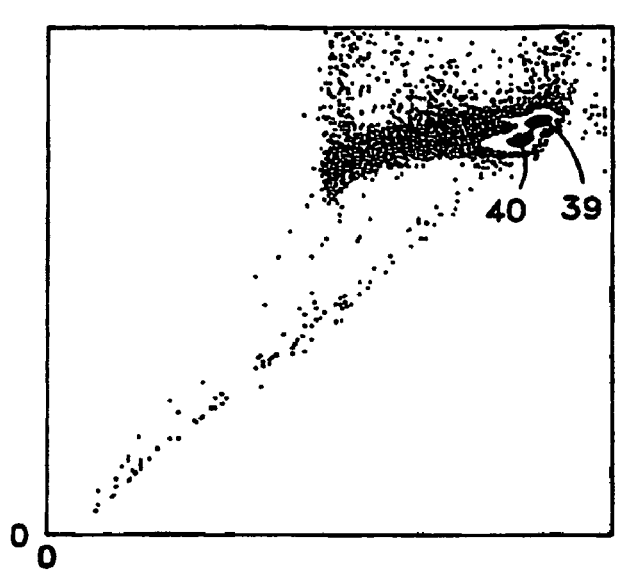
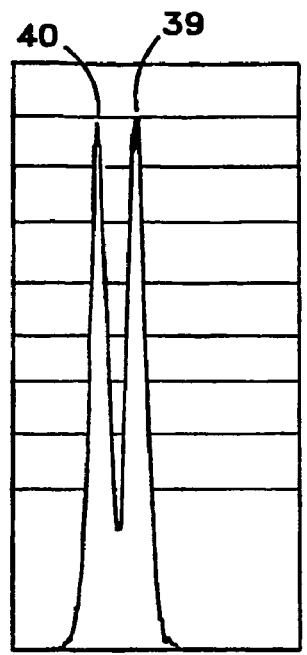
Fig. 5A
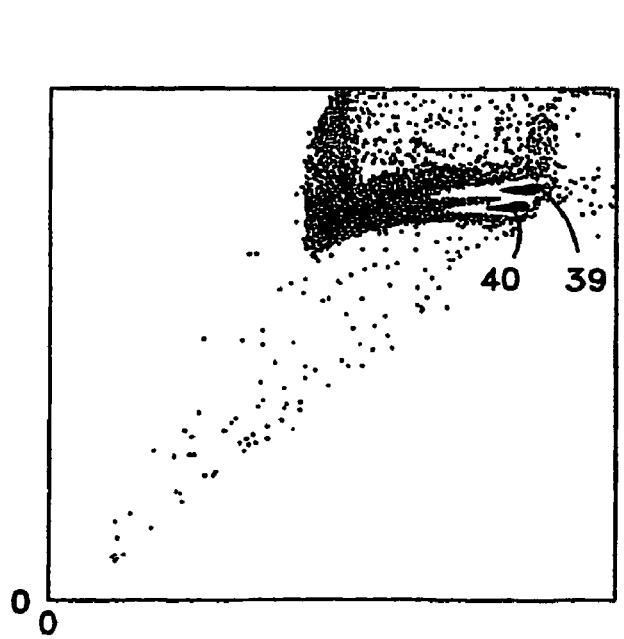
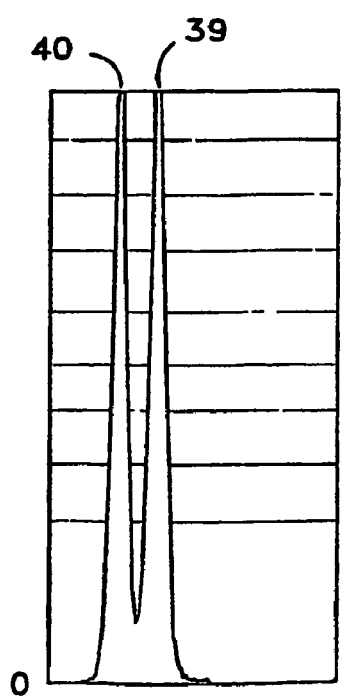
Fig. 5B

Fig 6
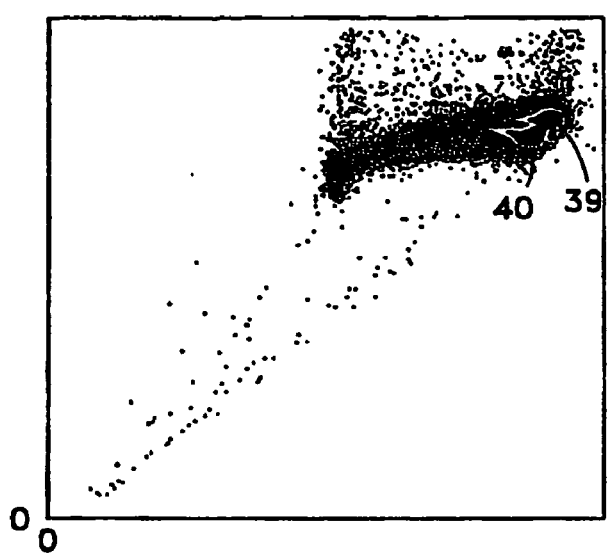
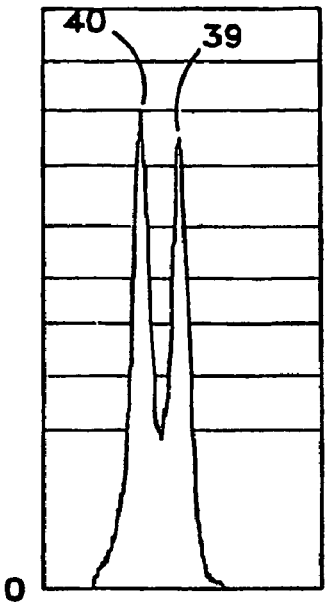
Fig. 6A
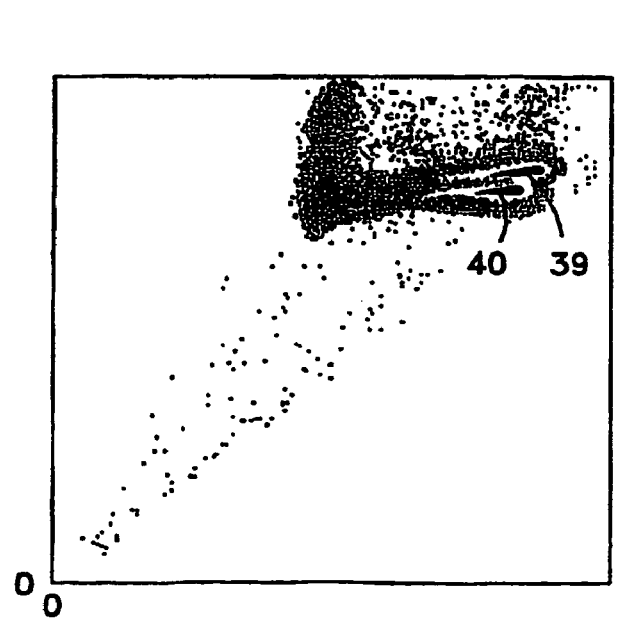
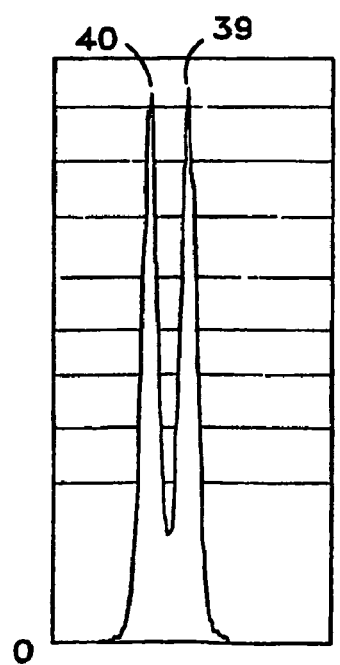
Fig. 6B

Fig 7
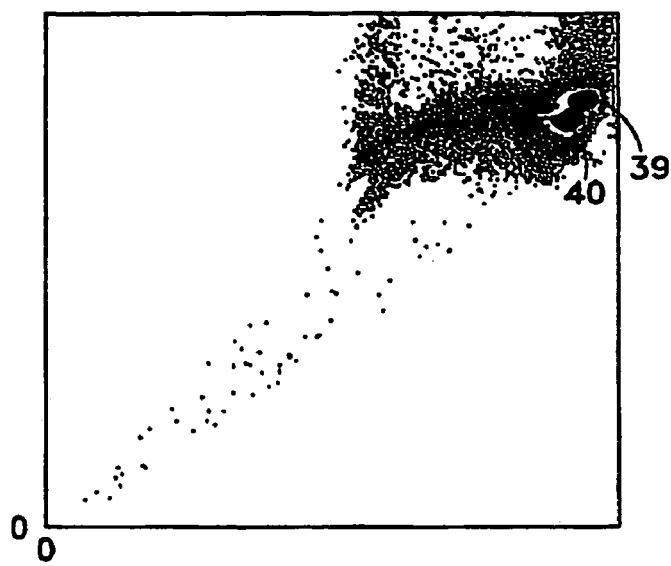
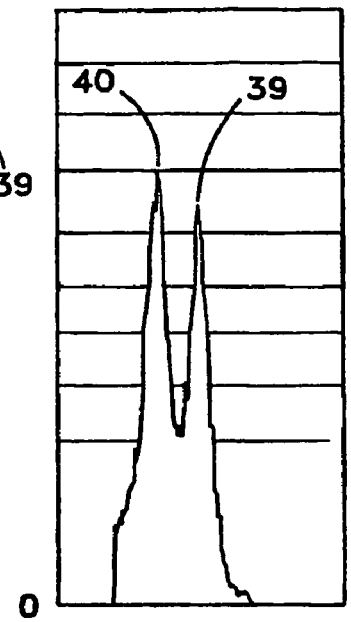
Fig. 7A
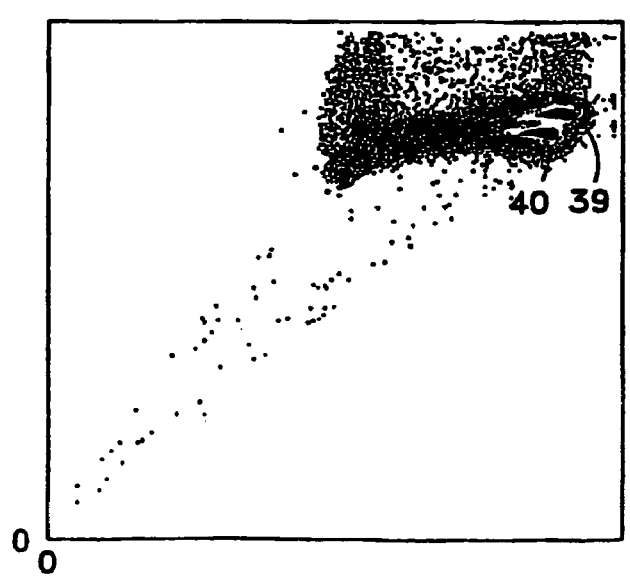
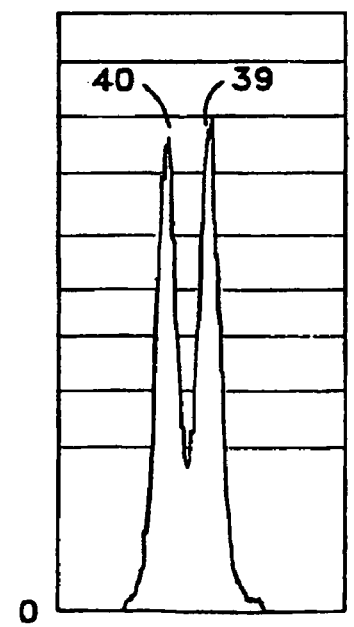
Fig. 7B

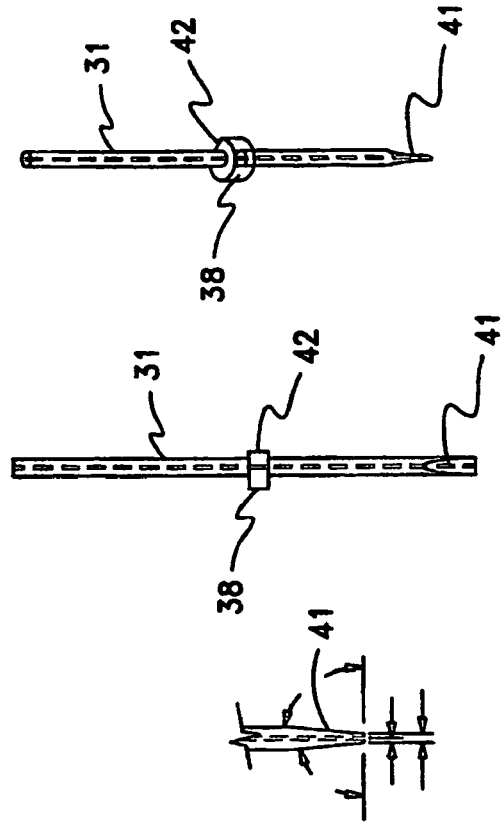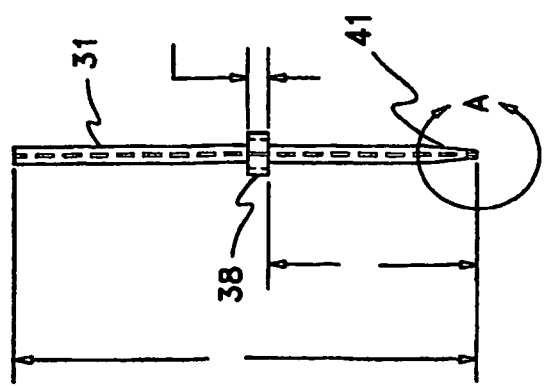
Fig. 8

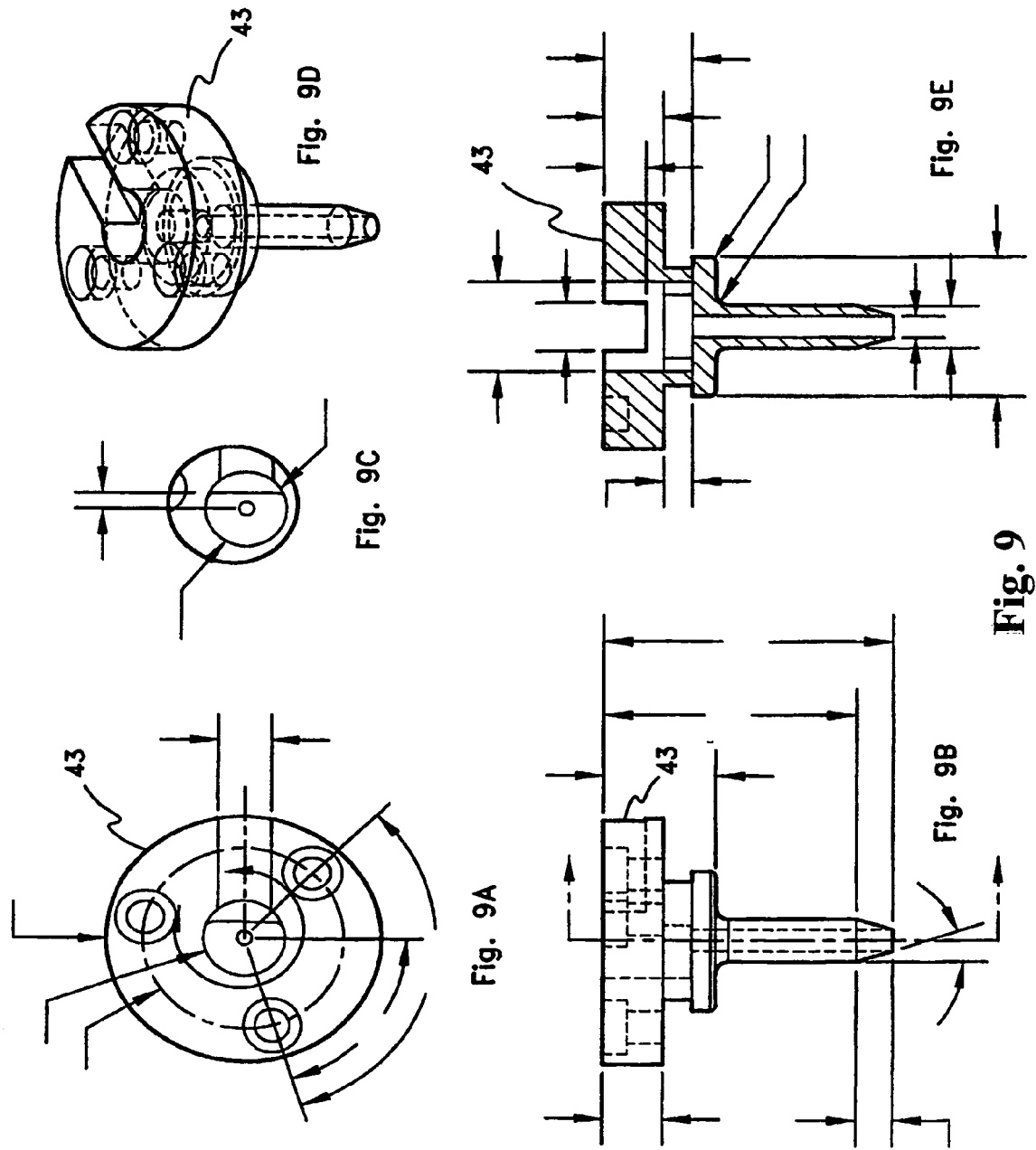

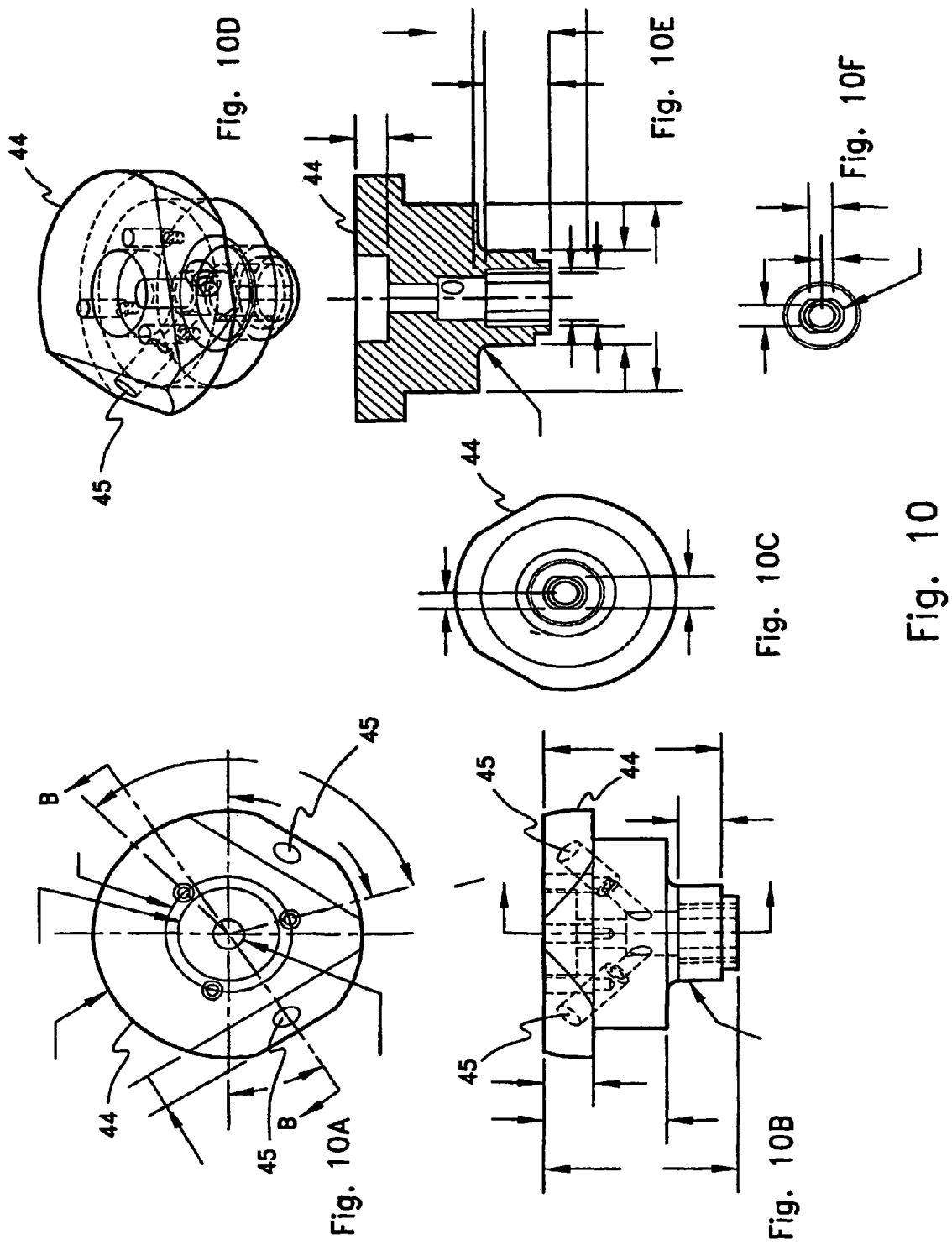

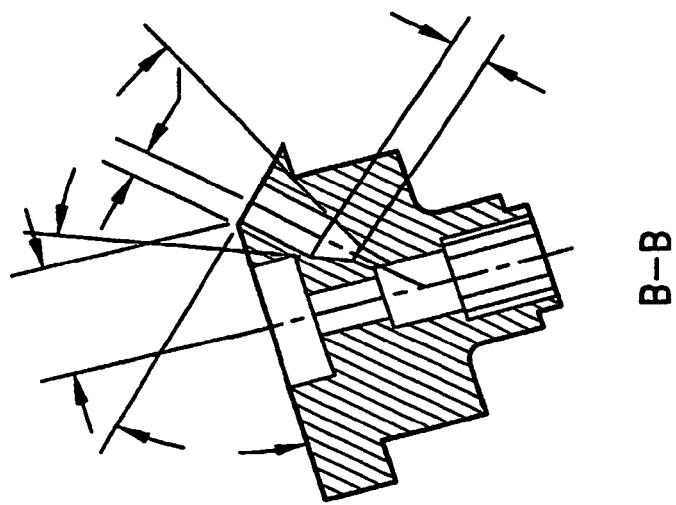
Fig. 11A
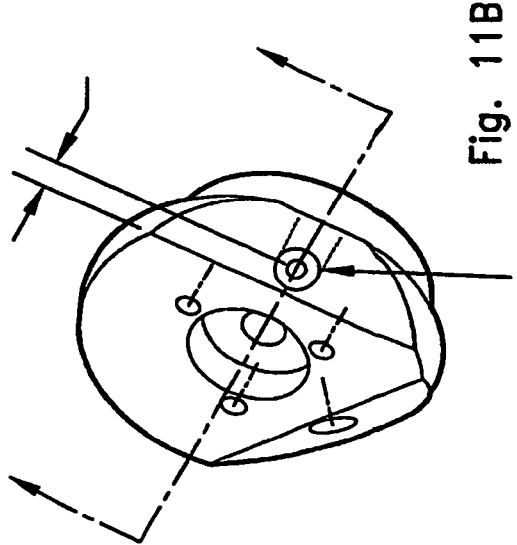
Fig. 11B
Fig. 11

HIGH RESOLUTION FLOW CYTOMETER

This United States patent application is a division of U.S. patent application Ser. No. 10/524,793, filed Oct. 20, 2005, which is a National Phase of International Patent Cooperation Treaty Application PCT/US2003/025812, filed Aug. 15, 2003, which claims the benefit of U.S. Provisional Patent Application No. 60/404,279, filed Aug. 15, 2002, each hereby incorporated by reference herein.

I. TECHNICAL FIELD

High resolution differentiation and separation of particles based upon particle characteristics. Specifically, high resolution differentiation and separation of sperm cells into X-chromosome bearing and Y-chromosome bearing populations or increased homogeneity.

II. BACKGROUND OF THE INVENTION

Effective preselection of sex has been accomplished in many species of mammal following the development of safe and reliable methods of separating sperm cells into enriched X chromosome bearing and Y chromosome bearing populations. Separation of X chromosome bearing sperm cells from Y chromosome bearing sperm cells can be accomplished as disclosed herein and as disclosed by various international patent applications, for example: WO 98/34094, WO 99/33956, WO 99/42810, WO 00/06193, WO 01/40765, WO 01/85913, WO 02/43486, WO 02/43574, each hereby incorporated by reference herein.

Now referring to FIGS. 1 and 2, a conventional technology flow cytometer provides a particle or cell source (1) that acts to establish or supply particles or cells (16) (which can be sperm cells or spermatozoa, sperm heads, commonly occurring blood cells such as leukocytes, lymphocytes, monocytes, neutrophils, basophils, macrophages, erythrocytes, platelets, or rare cell types such as fetal cells in circulation within maternal blood, cells which harbor viruses, cancer cells, and the like, as well as parts of cells such as organelles, mitochondria, individual chromosome, as well as man made particles such as beads or microspheres or nanospheres to which a biological component may be bound) that can be stained with at least one fluorochrome for analysis. The particles or cells (16) are introduced within a nozzle (2) in a manner such that the particles or cells (16) are introduced into a fluid stream or sheath fluid (3). The fluid stream (3) is usually supplied by some fluid source (4) so that as the particle or cell source (1) supplies the particles or cells (16) into the fluid (3) they are concurrently fed through the nozzle (2).

In this manner, the fluid stream (3) forms a fluid environment for the particles or cells (16). Since the various fluids are provided to the flow cytometer at some pressure, they exit out of nozzle (2) at a nozzle orifice (5). By providing some type of oscillator (6) which may be very precisely controlled through an oscillator control (7), pressure waves may be established within the nozzle (2) and transmitted to the fluid stream (3) exiting the nozzle (2) at nozzle orifice (5). Since the oscillator (6) acts upon the sheath fluid (3), the fluid stream (8) formed below the nozzle orifice (5) eventually and regularly forms drops (9). Since particles or cells (16) are surrounded by the fluid stream (8) formed below the nozzle orifice, the drops (9) may entrain within them individually isolated particles or cells (16).

Since the drops (9) can entrain individual particles or cells (16), a flow cytometer can be used to separate such particles or cells (16) based upon particle or cell characteristics. This is accomplished through a particle or cell sensing system (10). The particle or cell sensing system involves at least some type of detector or sensor (11) that responds to the particles or cells (16) contained within fluid stream (8). The particle or cell sensing system (10) may cause an action depending upon the relative presence or relative absence of a characteristic, such as fluorochrome bound to the particle or cell or component thereof, such as DNA or lipfds, or mitochondria, or organelles within the cell, that may be excited by an irradiation source such as a laser (12) generating an irradiation beam to which the particle or cell (16) can be responsive.

While each type of particle, cell, or component thereof may be stained with at least one type of fluorochrome, different amounts of fluorochrome(s) bind to each individual particle or cell (16) based on the number of binding sites available to the particular type of fluorochrome used. With respect to spermatozoa, as but one example, the availability of binding sites for Hoechst 33342 stain is dependant upon the amount of DNA contained within each spermatozoa. Because X-chromosome bearing spermatozoa contain more DNA than Y-chromosome bearing spermatozoa, the X-chromosome bearing spermatozoa of a species of mammal can bind a greater amount of fluorochrome than the corresponding Y-chromosome bearing spermatozoa of the same species of mammal. Thus, by measuring the fluorescence emitted by the bound fluorochrome upon excitation, it can be possible to differentiate between X-bearing spermatozoa and Y-bearing spermatozoa.

In order to achieve separation and isolation based upon particle or cell characteristics, emitted light can be received by sensor (11) and fed to some type of separation discrimination system (13) coupled to a droplet charger which differentially charges each droplet (9) based upon the characteristics of the particle or cell (16) contained within that droplet (9). In this manner the separation discrimination system (13) acts to permit the electrostatic deflection plates (14) to deflect drops (9) based on whether or not they contain the appropriate particle or cell (16).

As a result, a flow cytometer acts to separate individual particles or cells (16) entrained in drops (9) by causing them to be directed to one or more collection containers (15). For example, when the separation discrimination system (13) differentiates sperm cells based upon the relative amounts of DNA contained by X-chromosome bearing spermatozoa and Y-chromosome bearing spermatozoa, the droplets entraining X-chromosome bearing spermatozoa can be charged positively and thus deflect in one direction, while the droplets entraining Y-chromosome bearing spermatozoa can be charged negatively and thus deflect the other way, and the waste stream (that is droplets that do not entrain a particle or cell (16) or entrain undesired or unsortable cells) can be left uncharged and thus may be collected in an undeflected stream. Numerous deflection trajectories can be established and collected simultaneously with some conventional flow cytometers.

Even though conventional flow cytometers for the separation of cells or particles have been improved over the past several years significant problems still remain with respect to the resolving capacity of convention flow cytometers.

A significant problem with conventional flow cytometer technology as shown by FIG. 1 may be that the fluid source (4) along with the associated fluid source conduit(s) (23) introduces fluid (3) into the nozzle (2) substantially perpendicular to the flow of the fluid (3) within the nozzle (2). These two directions of flow can interrupt, distort, or delay formation of laminar flow within the nozzle (2). Certain particles or cells (16), being large in comparison to the molecules of the fluid stream, and particularly in cases where the positioning, orientation, and inter-particle distribution is critical to accurate analysis of individual particles or cells (16), and correct entrainment of individual particles or cells (16) into individual drops (9) is required, are strongly influenced by fluid movement which may be turbulent, and therefore maintaining laminar flow is an important aspect, which has been overlooked in the design of conventional flow cytometer technology. It is also noteworthy that the oscillator (6) which serves the primary function of providing pressure waves to allow the formation of individual drops (9), will also provide standing waves of pressure within the nozzle (2) which will influence the laminar flow characteristics, especially as improper nozzle design can lead to harmonic divergences such as pressure beats or sub-oscillations.

A second significant problem with conventional flow cytometer technology as shown by FIG. 1 may be that the cell source conduit (17) between the cell source (1) and the nozzle (2) is not straight. A substantial bend in the cell source conduit (17) can result in a change in fluid pressure in response to the bend in the cell source conduit or can create fluid streams having areal cross sections that exhibit disparate stream velocity. This problem can be exacerbated by cells or debris aggregating at the bend(s) in the cell source conduit (17).

A third significant problem with conventional flow cytometer technology as shown by FIG. 1 may be that the cell source conduit (17) is too long. Conventional flow cytometer cell source conduit (17) from the cell source (1) to the injection point (18) of particles or cells into the fluid stream can be greater than four inches in length. Conventional length cell source conduit (17) can cause cells to settle or aggregate in, or flow through, the cell source conduit in a manner that increases turbulent flow, and therefore decreases apparent resolution of cell populations.

A fourth significant problem with conventional flow cytometer technology as shown by FIG. 1 may be that the cell source conduit (17) and in particular the particle injector (19) portion of the cell source conduit may not be individually replaceable. As such, a failure, or reduced performance, of the cell source conduit (17) or the particle. injector (19) portion can result in the necessity to replace the entire nozzle (2) and the cell source conduit (17) along with any other component of the flow cytometer inseparably joined to the nozzle (2).

A fifth significant problem with conventional flow cytometer technology can be that there may be a connector (20) mounted to the entry end of the particle injector (19) portion of the cell source conduit (17) to couple the injector portion (19) with the cell source fluid conduit (17). Even zero-dead volume connectors or couplers can introduce sufficient deformation or non-concentricity to the cell source conduit interior surface to allow particles or debris to adhere, cling, attach, or otherwise become immobilized at the location of the connector (20) resulting in potential cross contamination between sample populations transferred in the cell source fluid stream, or causing restrictions or otherwise altering the configuration of the cell source fluid path.

A sixth significant problem with convention flow cytometer technology can be that the interior surfaces of the cell source conduit (17) or the interior surfaces of the injector (19) portion of the cell source conduit (17) are sufficiently rough or uneven to reduce apparent resolution of mixed populations of cells or particles. One aspect of this problem can be that surface features that result in the rough or uneven surface can on occasion break away from the cell source conduit interior surface and can become lodged in the flow path. In some cases, restriction or occlusion of the cell source conduit (17) can result. Another aspect of this problem can be that particles interact with the rough or uneven features of the cell source conduit to create asymmetries in the velocity of the fluid stream, which can introduce sheer forces or turbulent flow properties that decrease apparent resolution of cell populations.

A seventh significant problem with conventional flow cytometry technology can be that areal cross sections of the nozzle (2) can be too large. The larger the area of the cross section of the nozzle (2), the greater the area on which bubbles or debris or particles (16) can attach and interfere with the fluid dynamics within the nozzle assembly, and the greater the complexity of standing pressure waves and sub-harmonic pressure waves which may be stabilized in the nozzle (2).

An eight significant problem with conventional flow cytometery may be that the body of the nozzle (2) comprises a first nozzle body element (21) and a second nozzle body element (22). This can create an interior surface of the nozzle having sufficient distortion or roughness to disrupt or diminish the laminar flow of the fluid stream which can translate into reduced resolving capacity of conventional flow cytometer(s), or if the two fabrication materials of a first nozzle body element (21) and a second nozzle body element (22) have different elasticities, they may each deliver pressure waves from the oscillator (6) with different sub-harmonic characteristics, which may tend to distort laminar flow in the critical area of the particle flow path just prior to exiting the nozzle (2) at the orifice (5).

A ninth significant problem in the conventional flow cytometry technology relates to the difficulty in accurate measurement of DNA in particles or cells, such as live mammalian sperm, which bind different amounts of fluorochrome based on known differences in DNA content, and yet have large coefficients of variation which obscure the measurement For example, as shown by Johnson et al., Theriogenology, Vol. 52, No. 8, 1326 (1999) the effect of the size of an X chromosome on total DNA content of a live sperm cell in comparison to the effect of the Y chromosome size on the total DNA of a live sperm cell is determined by the differences between the sizes of an X and a Y chromosome in a specific mammalian species, as well as the actual amount of DNA (numbers and sizes of all other chromosomes). And specifically (X-Y)/X of: 2.8% in humans, 3.0% in rabbits, 3.6% in boars (pig), 3.7% in stallion (horse), 3.8% in bull (cattle), 3.9% in dog, 4.2% in ram (sheep), and as much as 7.5% in chinchilla. Welch et al. show, however, that the coefficient of variation (CV) in the analysis of sperm by conventional methods is considered good vat 0.9% and can even be as high as 1.97%. Welch et al., Theriogenology, Vol. 52, No. 8, 1348 (1999) Thus, especially for species such as humans with very low (X-Y)/X values of 2.8%, it is critical to reduce the CV to lower than 1%, and preferably to as close to zero as possible. The definition of resolution, as used in the description of the instant invention, refers to the capability of the instrument in resolving of sperm into two populations based on the proximity of the measured value from each single sperm to a known value, with the primary negative determinant being a high CV for the population being analyzed.

The instant invention addresses the variety of problems associated with reduced resolution of conventional flow cytometer instruments in separating flow separable particles or cells (16), cells, and specifically sperm cells into enriched populations based upon particle characteristics, or in the context of sperm cells into enriched X-chromosome bearing and Y-chromosome bearing populations.

III. DISCLOSURE OF THE INVENTION

Accordingly, the broad object of the invention can be to provide an increased resolution flow cytometer which can afford increased homogeneity of isolated populations differentiated by one or more particle characteristics.

A first aspect of this object of the invention can be to introduce fluids from the fluid source (4) the into the nozzle (2) in a manner that reduces disruption, turbulence, distortion, or delay of formation the laminar flow of the fluid stream (3) within the nozzle (2) or establishing a laminer flow with the core stream containing particles or cells (16) introduced into the nozzle at the injection point (18).

A second aspect of this object of the invention can be to provide a cell source fluid stream between the cell source (1) and injection point that maintains a substantially constant areal velocity with respect to a cross section of the cell source fluid stream within the cell source conduit (17), or that substantially eliminates changes in velocity of the cell source fluid stream due to curvature, deformation, or bends in the cell source, or reduces impediments, obstructions, or particle aggregation or collect areas within the cell source conduit (17).

A third aspect of this object of the invention can be to provide an adjustable cell source fluid stream configuration that provides with respect to a particular type of particle or the type of particle differentiation characteristic, a cell source fluid stream volume that maintains consistency with respect to the flow of particles (16) from the cell source (1) to the injector point (18).

A fourth aspect of this object of the invention can be to provide an adjustable coaxial fluid stream that provides with respect to a particular type of particle, or with respect to a particular of type of particle differentiation characteristic, a core stream containing particles (16) within the fluid stream (8) formed below the nozzle orifice (5) that has greater consistency.

A fifth aspect of this object of the invention can be to provide a particle injector portion (31) of cell source conduit (28) that is replaceable.

A sixth aspect of this object of the invention can be to eliminate the connector (20) mounted to the entry end of the injector (19) portion of the cell source conduit (17).

A seventh aspect of this object of the invention can be to eliminate or substantially reduce the roughness or unevenness of the interior walls of the cell source conduit (17).

An eighth aspect of this object of the invention can be to provide a continuously integral one-piece nozzle to substantially eliminate or reduce non-concentricity of interior circular areal cross sections of the nozzle, or substantially eliminate or reduce deformations to the interior surface of the nozzle.

Another significant object of the invention can be to provide devices or methods of separating sperm cells that can maintain greater viability of mammalian sperm cells throughout a flow-sorting process.

Naturally, further significant objects of the invention are made clear in the proceeding description and drawings.

IV. BRIEF DESCRIPTION OF THE DRAWINGS

FIG. 2 shows a schematic representation of conventional flow cytometer technology.

Figure 1:
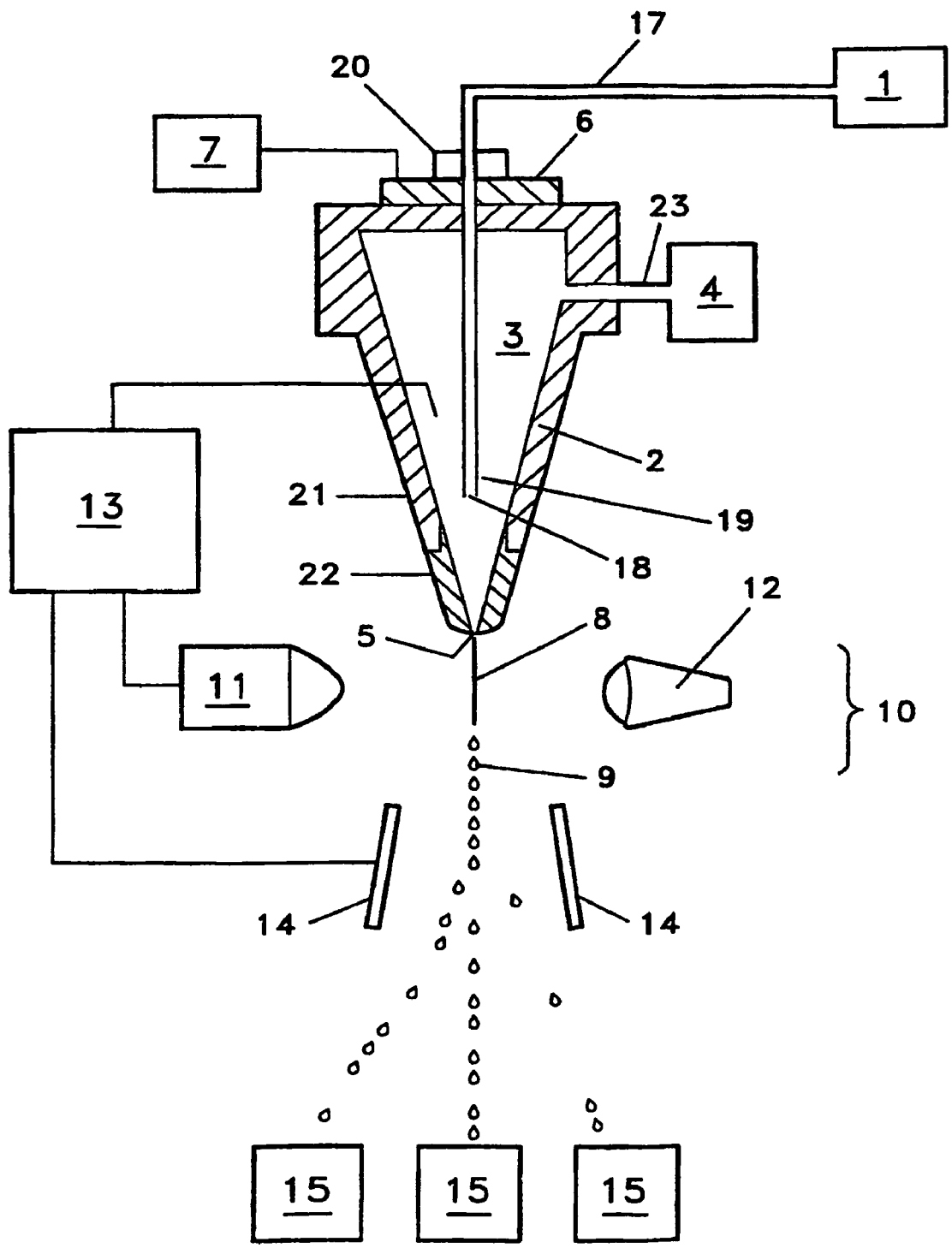
FIG. 1 shows a schematic representation of conventional flow cytometer technology.

FIG. 4 provides a comparison of a conventional flow cytometer nozzle assembly (FIG. 4a) and the injector portion of conventional flow cytometer (FIG. 4b) with the corresponding resolution enhanced flow cytometer nozzle assembly invention (FIG. 4c) and the resolution enhanced injector portion of the enhanced resolution flow cytometer invention (FIG. 4d).

FIG. 5 provides a comparison of the resolution of a bovine sperm nuclei sample using conventional flow cytometer technology (FIG. 5a) and resolution of the same bovine sperm nuclei sample using the enhanced resolution flow cytometer invention FIG. 5b) each at 25,000 events per second.

FIG. 6 provides a comparison of the resolution of a bovine sperm nuclei sample using conventional flow cytometer technology (FIG. 6a) performed at 50,000 events per second and resolution of the same bovine sperm nuclei sample using the enhanced resolution flow cytometer invention FIG. 6b) performed at 60,000 events per second.

FIG. 7 provides a comparison of the resolution of a bovine sperm nuclei sample using conventional flow cytometer technology (FIG. 7a) performed at 100,000 events per second and resolution of the same bovine sperm nuclei sample using the enhanced resolution flow cytometer invention (FIG. 7b) performed at 110,000 events per second.

FIG. 8 shows a particular embodiment of the particle injector invention.

FIG. 9 shows a particular embodiment of an inner nozzle body invention.

FIG. 10 shows a particular embodiment of an outer nozzle body invention.

FIG. 11 provides cross section B-B of the particular embodiment of the outer nozzle invention shown in FIG. 10.

V. MODE(S) FOR CARRYING OUT THE INVENTION

The invention involves a high resolution flow cytometer that can increase resolving power to separate mixed populations of cells, sperm cells, or particles from each other based upon various cell or particle characteristics individually or in combination.

As such, while particular examples of the invention are provided that describe the invention in the context of separating sperm cells, or separating bovine or equine intact live sperm cells, it should be understood that the enhanced resolution technologies described can have application with respect to separation of various types of flow separable particles, including, but not limited to, cells, spermatozoa, or sperm nuclei, collected, handled, or stored in a variety of ways.

X-chromosome bearing and Y-chromosome bearing populations of spermatozoa should further be understood to encompass enriched populations of flow separated or sorted spermatozoa obtained from a male of a species of mammal including, but not limited to, spermatozoa from humans; as well as other mammals such as bovids, equids, cervids, ovids, canids, felids, goats, swine, or camels; as well as marine mammals, such as cetaceans (various species of whales or porpoises); and specifically including endangered mammalian species; and particular individuals of a species that may be zoological specimen(s), rare or prize specimen(s), or a specimen of a species of mammal that provides semen for use in animal husbandry, herd management systems, artificial insemination protocols, cryogenic storage, or for example a species of mammal listed by Wilson, D. E. and Reeder, D. M., Mammal Species of the World, Smithsonian Institution Press, (1993), hereby incorporated by reference herein.

This list of animals is intended to be exemplary of the great variety of mammals from which spermatozoa can be obtained or which can be flow sorted with the enhanced resolution flow cytometer invention described herein and it is not intended that the high resolution or enhanced resolution aspects of the invention be limited to the analysis or the flow separation of any particular type of particle or the spermatozoa from any particular species of mammals or individual mammal.

Cells, spermatozoa, or particles obtained using the enhanced resolution flow cytometry invention described herein can be incorporated into various applications or products including but not limited to artificial insemination protocols or as part of commercial business methods such as those as described in Patent Cooperation Treaty Application Nos. PCT/US01/18879 or PCT/US99/17165; or be used with low dose insemination protocols as described in Patent Cooperation Treaty Application No. PCT/US98/27909, or used with in-vitro fertilization of oocytes from animals, including humans, as described in Patent Cooperation Treaty Application No. PCT/US01/45237, each of the above-mentioned applications or documents hereby incorporated by reference.

The use of the term purity should be understood to be the percent of the isolated spermatozoa population bearing a particular differentiating characteristic or desired combination of characteristics. For example, where a population of spermatozoa are separated based upon bearing an X-chromosome as opposed to a Y-chromosome, a X-chromosome bearing population having 90% purity comprises a population of spermatozoa of which 90% of the individual spermatozoa bear an X-chromosome while 10% of such population of spermatozoa may bear a Y-chromosome. As such, purity with respect to X-chromosome bearing populations or Y-chromosome bearing populations of spermatozoa generated in accordance with the invention can comprise a purity greater than achieved with convention flow separation devices or can comprise a purity of between about 70% to about 99%, or can be selected from the group consisting of between 90% to about 100%, between about 91% to about 100%, between about 92% to about 100%, between about 93% to about 100%, between about 94% to about 100%, between about 95% to about 100%, between about 96% to about 100%, between about 97% to about 100%, between about 98% to about 100%, between about 99% to about 100%.

Importantly, while this description includes numerous embodiments of the invention some of which may include isolated X-chromosome and Y-chromosome bearing populations of spermatozoa, and while the description further discloses specific aspects of enhanced resolution spermatozoa separation devices or methods of how to enhance resolution of mixed populations of spermatozoa, the basic concepts of the invention should be understood to be applicable to other types of particles or events having similar or different particle differentiation characteristics or event differentiation characteristics. It should be understood that the invention can be applicable to a variety of circumstances including those in which enhanced resolving capacity of small differences in photogenerated signal may be necessary.

Moreover, while this disclosure provides descriptions of embodiments of apparatus and methods for flow separation of X-chromosome bearing spermatozoa from Y-chromosome bearing spermatozoa, the description of these embodiments of the invention is not meant to reduce the scope of the invention to only flow separation of spermatozoa or only to high or enhanced resolution flow cytometer spermatozoa separation systems but rather these examples are intended to exemplify the basic concepts of the invention in a practical manner so that they may be applied to the wide variety of particles or applications.

Figure 3:
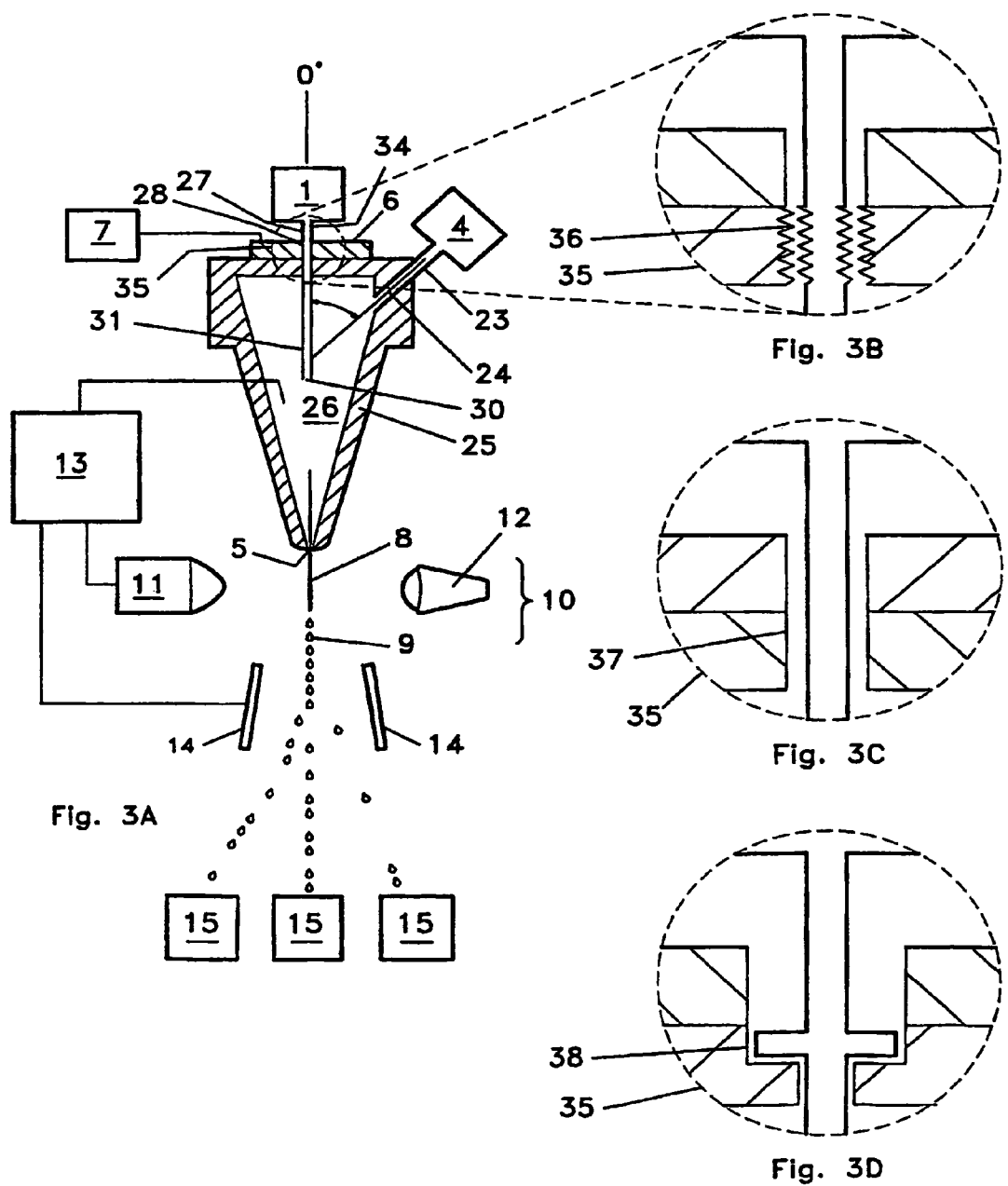
FIG. 3 shows a particular embodiment of the enhanced resolution flow cytometer invention.

Now referring primarily to FIG. 3, the invention can comprise at least one fluid source conduit (23) that introduces a fluid source stream (24) into the enhanced resolution nozzle (25) at an angle relative to fluid stream (26) flow within the nozzle (25) that enhances particle resolution by the cell sensing system (13). The angle of introduction can vary depending on the type of particle populations being differentiated. With respect to some embodiments of the invention, the fluid source conduit (23) can introduce the fluid source stream (24) at an angle between about zero degrees to about 45 degrees with respect to the central longitudinal axis of the enhanced resolution nozzle (25). With respect to certain embodiments of the invention, a plurality of fluid source conduits (23) can introduce a plurality of fluid source streams (24) into the enhanced resolution nozzle (25).

Again referring primarily to FIG. 3, the invention can further comprise a symmetrical velocity cell source fluid stream (27) within the cell source conduit (28). A symmetrical velocity cell source fluid stream provides cell source fluid stream (27) having a velocity that achieves substantially symmetry across the perpendicular cross section of the cell source fluid stream (27) which can include the anticipated symmetry associated with the reduction in velocity near or at the interior surface of the cell source conduit (28), but avoids or reduces asymmetries of velocity across a perpendicular cross section of the cell source fluid stream (27). To establish this symmetry in velocity of the cell source fluid stream (27), certain embodiments of the invention can utilize a substantially linear cell source conduit (28). A linear cell source conduit (28) presents a linear flow path or more linear flow path than conventional technology to the cell source fluid stream (27) without any substantial curvature, bends, or turns that may upon negotiation by the cell source fluid stream (27) require a portion of the cell source fluid stream (27) to reduce velocity or a portion of the stream to increase velocity. As such, as compared to conventional technology the symmetrical velocity cell source fluid stream (27) provides a solution to the problems described below with conventional type cell source fluid streams (29), as shown in FIG. 1.

Now referring to the convention technology illustrated by FIG. 1, when stream velocity is not symmetrical, cells introduced into the cell source fluid stream (29) can travel at different rates respectively and the initial distribution of the particles by the cell source (1) into the conventional cell source fluid stream (27) can be effected resulting in a substantially different distribution of cells presented at the injection point (18) that can effect the apparent resolution of particle populations.

Of particular problem with conventional technology, the cell source conduit (17) can have, for example, a 90.degree. bend necessitating the conventional cell source fluid stream (29) to respond to a small radius curvature or bend. At the turn, cell source fluid stream (29) velocity may abruptly drop across the entire cross sectional area of the cell source fluid stream (29) or a portion thereof. This reduction in cell source stream (29) velocity may with respect to the smaller interior radius of the bend be substantially reduced with respect to the velocity of the stream adjacent to the larger exterior radius. This can in some circumstances result in particles that accumulate or aggregate at the curvature or bend in the cell source conduit (17) that can further exacerbate asymmetry in the cell source fluid stream (29) and further interfere with the distribution of particle delivery at the injection point (18). In some instances, the particles may interrupt flow of the cell source fluid stream (29) in part or all together resulting in failure of the flow separation events entirely.

Some embodiments of the invention can include independently or in combination with other aspects of the invention a limited resistance interface surface between the cell source fluid stream (27) and the interior of cell source conduit (28).

The limited resistance interface surface with respect to materials such as plastic or metal can comprise a polished or smoothed interior surface of the cell source conduit (28). The interior surface(s) can be polished or smoothed until the observed resolution increase reaches a maximum, or desired amount. Alternately limited resistance or distortion of the interface surface can be accomplished by substitution of materials that are used to manufacture the cell source conduit (28). For example, glass tube or Teflon® tube, can be substituted for metal or other types of plastic tube. A limited resistance cell source conduit (28) can be further accomplished by chemical treatment of the interior surface of the cell source conduit (28). In these embodiments of the invention, plastics or glass for example can be silanized, while metals can be further passified by acid wash.

Again referring primarily to FIG. 3, embodiments of the invention can include an cell source fluid stream (27) having adjusted coaxial fluid stream characteristics. Because resolution of particles can be dependent upon fluid stream characteristics generated by operating parameters such as temperature, stream velocity, stream pressure, configuration of conduits in which the fluid stream flows, injection point of particles in the stream, type of particle injected into the stream, or the like, it can be important to control stream characteristics to achieve, maintain, or enhance resolution of particle populations. As such, the diameter or length of the cell source conduit (28), and location of the injection point (30) within the nozzle (25) of the cell source fluid stream (27) can each, or in combination, effect resolution of particle populations.

As to some embodiments of the invention particle injector (31) can have a selectably variable adjustment element (35) which allows adjustment or alteration of the distance between the nozzle orifice (5) and the location in the fluid stream (26) at which the particle injector (31) entrains particles (16) delivered from cell source (1). Selectably variable adjustment of the particle injector (31) allows alteration of fluid stream characteristics in compensation for a change of operation conditions from a first set of operating conditions to a second set of operating conditions whether the change in operation conditions comprises a change in sheath fluid, species of sperm cell, temperature, fluid stream pressure, fluid stream temperature, or otherwise. Importantly, by adjusting the distance between the particle injector (31) and the nozzle orifice (5) increased resolution based on a characteristic of cells can be achieved. With respect to sperm cells, increased resolution of sperm cells separated based upon bearing an X-chromosome or a Y-chromosome can be achieved utilizing the invention, as shown by FIGS. 5-7.

Selectable variable adjustment of the particle injector (31) to allow adjustment of the injection point (30) can be accomplished in a variety of ways. First, as shown by FIG. 3*b*, a pair of mated spiral threads (36) engaged between the particle injector (31) and the nozzle body (25) can provide rotational adjustment of the particle injector (31) to alter the location of the injection point (30). Second, as shown by FIG. 3*c*, adjustable engagement can be provided between the particle injector (31) and the nozzle body (25) by providing slidable engagement (37). Third, as shown by FIGS. 3, 4*d*, and 8 a plurality of interchangeable particle injectors (31) can have alternate lengths established by at keyed stop (38) mated with the nozzle body (25).

Now referring primarily to FIGS. 3 and 4, the invention can further comprise a single piece nozzle (25) (FIG. 4*d*). Unlike the nozzle (2) shown in FIGS. 1 and 4*a*, the instant invention can eliminate non-concentricity that can occur during mating of two or more discrete nozzle elements, such as the first nozzle element (21) and the second nozzle element (22) as shown in FIGS. 1 and 4*b*.

Again referring primarily to FIGS. 3 and 4, the invention can further comprise a compression sleeve coupler (32) to replace the connector (20) included in conventional technology. An embodiment of the compression sleeve coupler (32) can comprise the terminal end of the cell source conduit (28) which has sufficient resiliently elastic properties to couple with the particle injector (31) tube. This embodiment of the invention can comprise a cell source conduit comprising Silastic® or other material having Silastic® like properties, or a cell source conduit (28) have sufficient elastic properties, such as Teflon® or resiliently elastic properties such as Tygon® to conform to the exterior surface of the particle injector (31) tube.

Now referring primarily to FIGS. 4*a* through 4*d*, a conventional nozzle assembly (FIGS. 4*a* and 4*b*) are shown in comparison with the invention (FIGS. 4*c* and 4*d*). As can be understood by the comparison of FIG. 1 and FIG. 3 and FIG. 4*b* and FIG. 4*d*, the conventional technology necessitates use of a longer flow path between the cell source (1) and the injection point (18) (see longer particle injector tube FIG. 4*b*) and a longer fluid stream path (3) between the fluid source and the injection point (18). The longer flow paths utilized by the conventional technology contribute to operation conditions which reduce resolution of different cell populations as shown by FIGS. 5*a*, 6*a*, and 7*a* as compared to shorter flow path utilized by the invention which contributes to operation conditions which increase resolution of different cell populations as shown by FIGS. 5*b*, 6*b*, and 7*b*.

With respect to some embodiments of the invention, a reduced length cell fluid stream (27) can be achieved by shortening the total length of the cell source conduit (28) between the cell source (1) and the injection point (30) until maximum increased resolution is achieved. The distance between the cell source (1) and the injection point (30) can be made substantially shorter than conventional technology, and as shown in FIGS. 4*c* and 4*d* can be less than four inches in length With respect to particular configurations of the flow cytometer invention and in with respect to the type of particle populations being separated the various embodiments of the invention can be used independently and in combination to increase the resolution between populations of particles, cells, or sperm cells. Specifically, with regard to an embodiment of the invention used to separate bovine sperm cells as shown by FIGS. 5*b*, 6*b*, and 7*b*, the one piece nozzle (25) utilizing a shorter flow path from the cell source (1) to the injection point (30), but maintaining the injection point (30) at the same distance from the nozzle orifice (5) dramatically increases resolution between sperm cells bearing an X-chromosome (39) and sperm cells bearing a Y-chromosome (40). However, this example is not intended to limit the use of the adjustable injection point (30) invention when analyzing sperm cells to the location used for resolving populations of bovine sperm cells. With respect to embodiments of the invention in which sperm cells from other species of mammals are being analyzed the injection point may have to be more or less close to the nozzle orifice to increase resolution or to initially resolve a population of sperm cells.

Again referring primarily to FIG. 4, the invention can comprise a reduced areal fluid stream (26) within the nozzle (25). The cross sectional area of the conventional fluid stream within the nozzle (2) with respect to some embodiments of the invention (shown by FIGS. 4*a* and 4*b*) can be substantially reduced as shown for example by FIGS. 4*c* or and 4*d*). The reduced cross sectional area of the fluid stream (26), which when compared to the conventional technology as shown by FIGS. 4a and 4b (Cytomation SX MoFlo® nozzle) as a measure, can for some embodiments of the invention, be between one fourth and one sixth of the conventional cross sectional fluid stream area (33) or less. Moreover, the length of the conventional nozzle (2) can be substantially shortened as to some embodiments of the invention as shown by both FIGS. 4c and 4d to provide an shorter fluid stream flow path. Specifically, with regard to flow separation of bovine spermatozoa a reduced cross sectional flow stream area of about one fifth of the conventional technology shown by FIG. 4c.

Now referring primarily to FIGS. 5, 6, and 7, an example of the enhanced resolution flow cytometer invention used to differentiate X-chromosome bearing and Y-chromosome bearing bovine nuclei is exemplified.

The enhanced resolution flow cytometer invention was set up using the following conditions:
Fluid Stream Pressure: 50.0 psi
Nozzle Orifice: 70 . mu.m
Laser Power: 150 mW
Photomultiplier Tube Volts: 220/230 V
Standard: Fresh Bull Nuclei
Sample: Equinox Lot #19901

However, lower fluid stream pressure of between 30 and 40 psi can be used with substantially the same results and increased fertility of sperm cells.

As can be understood from FIGS. 5, 6, and 7 comparative data was taken using conventional flow cytometer technology (FIGS. 5a, 6a, and 7a) and the high resolution flow cytometer invention (FIGS. 5b, 6b, and 7b) at three different event rates of about 25,000 events per second, about 50,000 to about 60,000 events per second, or about 100,000 to about 110,000 events per second. When a spermatozoa stained with a fluorochrome emits a detectable fluorescent emission, an event is counted. The greater the event rate typically the more difficult it can be to differentiate sperm cells based on the difference in magnitude of the detected fluorescent emission. With respect to all event rates, the mixed populations of X-chromosome bearing and Y-chromosome bearing bovine nuclei were differentiated to a greater extent using the high resolution flow cytometer invention as described herein.

Now referring primarily to FIGS. 8 to 11 which show components of an embodiment of the invention. FIG. 8 shows an embodiment of the interchangeable reduced length particle injector (31) having a keyed stop which mates with the nozzle body (25). The beveled tip (41). As to some embodiments of the invention the particle injector can have a diameter of about 1 to about 2 millimeters and have an internal bore of about 0.2 to about 0.3 millimeters. The beveled tip can intersect the plane perpendicular to the longitudinal axis of the particle injector at about 84 degrees with the terminal end of the bevel having a width of about 0.5 to about 0.7 millimeters. The keyed stop (38) an comprise a flat (42 to make rotational orientation consistent.

FIGS. 9 and 10 shows an embodiment of a inner nozzle body (43) keyed with a flat to slidly accept and position the particle injector (31). The inner nozzle body (43) inserts into the outer nozzle body (44) shown by FIG. 10. The outer nozzle body further includes at least one (two in the embodiment of the invention shown by FIG. 10) flow path from the fluid source (45) and can be configured for compression fittings or leak proof fittings to join the fluid source conduit to the outer nozzle body (44).

FIG. 11 provides additional FIG. 11a which shows a cross section B-B through the outer nozzle body (44) showing a particular configuration of the sheath fluid path and additional FIG. 11b providing an perspective view of the outer nozzle body.

As can be understood from FIGS. 4c, 4d, 9 and 11, the single piece nozzle (25) engages the outer nozzle body (44) and can be held in place with retaining ring (45). The nozzle assembly invention can be used to replace the conventional nozzle technology shown by FIGS. 1, 2, 4a, and 4b to provide increased resolution as shown by FIGS. 6b, 7b, and 8b.

With respect to asymmetric particle types such as sperm cells the nozzle assembly invention can provide greater orientation of the asymmetric particles within the nozzle body which provides greater consistency in analysis, especially when analysis comprises determination of the amount of emitted fluorescent light or cell volume.

Additionally, the increased resolution can be achieved at very high event rates between 20,000 and 100,000 events per second depending on the type of particle, cell, or sperm cell being analyzed. As a result, a much higher number of sperm may be separated, sorted, collected or recovered each second. This approach yields more product per unit time, and reduces production costs per unit, as the cost of flow cytometer or cell sorter can be a large part of the overall cost of producing separated particles.

When nozzle assembly invention operates with a lower pressure fluid stream, separated or sorted sperm cells collected, even at sort rates greater than 1000 sorts per second can have increased motility, viability, and fertility (sperm cell fertility characteristics) and can as to some species of sperm cell have substantially the same sperm cell fertility characteristics as freshly collected sperm cells in semen.

Because of the increased resolution that can be achieved with the nozzle body assembly, purity of sorted particles can also be increased even at sort rates which are greater than those achieved with the conventional nozzle technology.

The instant nozzle assembly invention generates fewer events in which a partial or full occlusion of the particle injector ( ) occurs. As such, there is less time in which a typical flow cytometer or cell sorter cannot be operated.

The nozzle assembly invention allows, in the event of an occlusion in the injection tube, a rapid removal of the injection tube, without the need to disassemble or dismount the entire nozzle assembly. The injection tube may then be easily inspected, cleaned, and reinstalled, which results in much shorter periods of downtime for such cleaning events, and therefore results in more productive use of the sorting instrument.

The nozzle assembly invention also allows cleaning of the injection tube by an unskilled (or semi-skilled) operator, without the need for a technical repairman. This means the labor costs for the rectification of a partial or full injection tube occlusion event may be reduced. It also means that the operator may immediately rectify such an event without spending time searching for an appropriate repair person.

The nozzle assembly invention allows an operator to observe a loss in separation resolution and rectify it immediately. Using a conventional nozzle assembly, a partial occlusion may not create stoppage of the instrument, but as the occlusion builds, may result in a situation where the resolution function of the instrument is slowly lost, over many hours, days, or even weeks, and during the entire time in which a poorly resolving nozzle is operating, the instrument will typically produce a much lower purity product, or particularly may need to be run at much lower sorting rates, resulting in lesser amounts of product being produced (lower productivity). In practice, the lower productivity is often only noticed by the operator when a skilled technician changes or cleans the nozzle, and the immediate improvement is seen.

The ease of replacement of the injection tube can allow the injection tube to be an item which is used one time only, or for a very limited period of time. In certain uses of the flow cytometer, such as sorting materials such as human fetal cells, or human sperm cells, or human bone marrow cells, where complex and lengthy CIP (clean in place) protocols are needed to assure the elimination of cross contamination between samples, it is convenient and expedient if the CIP procedures may be substituted by replacement of all parts which come in contact with the sample, thereby requiring the replacement of the sample injection tube.

The shorter injection tube, and accompanying smaller nozzle of the instant invention prevent certain types of malformations of the tube such as bending during inspection or assembly, and allow the tube less freedom of motion (vibration) within the nozzle. This maintains the tip of the injection tube closer to the desired injection point within the nozzle, and reduces the number and amplitude of harmonic resonances of the tube within the specific nozzle geometry.

The linear shape of the injection tube in the instant invention allows the injection tube to be inserted more or less deeply into the nozzle, which allows a user to modulate the exact distance between the point in which the sample is injected into the fluid stream and the point of the orifice of the nozzle. By allowing the observation of resolution data to influence the decision on the positioning of the injection tube in the nozzle (feedback control loop), it is possible to establish an injection point location which may change dynamically as other aspects of the instrument operation or sample are changed.

Most nozzle assemblies are expensive components, which are often manufactured in small numbers, and by manufacturers who are not able to create perfectly identical subcomponents. Thus, in practice, each nozzle assembly must be carefully tested, and if not accurate may need to be rebuilt or even discarded. The instant invention simplifies many of the parts of the nozzle assembly, which facilitates a more reliable manufacturing process for various sub-components of the nozzle assembly, and which allows easy replacement of the injection tube which is one of the more common causes of a poorly functioning nozzle. All of this leads to lower manufacturing costs, and more effective use of parts, which in turn lead to reduction in the costs of maintaining one or more production instruments which are used in a 24 hour per day, 7 day per week (24/7) production setting.

The invention can further include an mammalian embryo or a mammal produced using spermatozoa isolated or treated using any of the embodiments of the invention, or can include a mammalian embryo or a mammal of predetermined sex produced using separated spermatozoa in accordance with the various embodiments of the invention, or can include a mammalian embryo or a mammal produced using a sperm cell insemination sample(s) prepared according to the invention having an enriched population of either X-chromosome bearing sperm cells or enriched population of Y-chromosome bearing sperm cells, or a mammalian embryo or a mammal produced in accordance with any embodiment of the invention in which a sperm cell insemination sample containing a low number of sperm cells compared to the typical number used to inseminate that particular species of mammal is used.

As can be easily understood from the foregoing, the basic concepts of the present invention may be embodied in a variety of ways. It involves high resolution sperm cell processing system(s) with certain embodiments configured to provide a high or enhanced flow cytometer system that can be used with a variety of particles, cells, or sperm cells including both techniques as well as devices to accomplish high resolution particle differentiation and separation into enriched populations based upon selected particle characteristics.

In this application, various sperm cell processing techniques are disclosed as part of the results shown to be achieved by the various devices described and as steps that are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for the full patent application. It should be understood that such language changes and broad claiming will be accomplished when the applicant later (filed by the required deadline) seeks a patent filing based on this provisional filing. The subsequently filed, full patent application will seek examination of as broad a base of claims as deemed within the applicant's right and will be designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "flow-sorter" should be understood to encompass disclosure of the act of "flow-sorting"—whether explicitly discussed or not—and, conversely, were there effectively disclosure of the act of "flow-sorting", such a disclosure should be understood to encompass disclosure of a "flow-sorter" and even a "means for flow-sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the sperm cell processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The invention claimed is:

1. A flow cytometer, comprising:
   a) nozzle body;
   b) a nozzle having a nozzle orifice coupled to said nozzle body;
   c) a particle injector within said nozzle which establishes an injection point at a distance from said nozzle orifice; and
   d) a particle injector adjustment element which axially varies said distance along the longitudinal axis between said injection point and said nozzle orifice within said nozzle of said flow cytometer.

2. The flow cytometer as described in claim 1, further comprising a fluid source fluidicly coupled to said nozzle.

3. The flow cytometer as described in claim 2, wherein said fluid source supplies a fluid stream which flows within said nozzle.

4. The flow cytometer as described in claim 3, further comprising a particle source fluidicly coupled to said particle injector.

5. The flow cytometer as described in claim 1, wherein said particle injector adjustment element comprises slidly adjustable engagement between said particle injector and said nozzle body.

6. The flow cytometer as described in claim 1, wherein said particle injector adjustment element comprises a pair of mated spiral threads rotatably engaged between said particle injector and said nozzle body.

7. The flow cytometer as described in claim 1, wherein said particle injector adjustment element comprises a pair of mated spiral threads rotatably engaged between said nozzle body and said nozzle.

8. The flow cytometer as described in claim 1, wherein said particle injector adjustment element comprises a first particle injector having a first injection point within said nozzle replaceable by a second particle injector having a second injection point within said nozzle.

9. The flow cytometer as described in claim 4, further comprising at least one particle delivered from said particle source to said particle injector, said at least one particle entrained in said fluid stream at said injection point within said nozzle.

10. The flow cytometer as described in claim 9, where said at least one particle comprises a cell.

11. The flow cytometer as described in claim 10, wherein said cell comprises at least one sperm cell.

12. The flow cytometer as described in claim 11, wherein said sperm cell is obtained from a non-human mammal selected from the group consisting of: a bovine mammal, an equine mammal, a ovine mammal, a canine mammal, a feline mammal, swine mammal, a marine mammal, and a deer mammal.

13. The flow cytometer as described in claim 3, wherein said fluid stream comprises a sheath fluid.

14. The flow cytometer as described in claim 13, wherein said sheath fluid comprises a sheath fluid having a buffer selected from the group consisting of: a citrate buffer, a phosphate buffer, and a HEPES buffer.

15. The flow cytometer as described in claim 11, wherein said at least one sperm cell comprises sperm cells of a first species of mammal and sperm cells of a second species of mammal, and wherein said particle injector adjustment element establishes a first injection point within said nozzle for said sperm cells of said first species of mammal and establishes a second injection point within said nozzle for said sperm cells of said second species of mammal.

* * * * *

UNITED STATES PATENT AND TRADEMARK OFFICE
CERTIFICATE OF CORRECTION

| | | |
|---|---|---|
| PATENT NO. | : 7,981,682 B2 | Page 1 of 1 |
| APPLICATION NO. | : 12/927620 | |
| DATED | : July 19, 2011 | |
| INVENTOR(S) | : Kenneth M. Evans | |

It is certified that error appears in the above-identified patent and that said Letters Patent is hereby corrected as shown below:

On the title page item (57), line 6,
Abstract: "...(24) that introduces 0 fluid source..." should be: "(24) that introduces a fluid source..."

col 9, ln 18: "... invention can include an cell..." should be: "...invention can include a cell..."

col 11, ln 58: "...with a flat to slidly accept..." should be: "...with a flat to slidably accept..."

claim 5, ln 20: "...element comprises slidly adjust-..." should be: "...element comprises slidably adjust..."

claim 12, ln 45: "...a ovine mammal..." should be: "...an ovine mammal..."

claim 12, ln 46: "...mammal, swine mammal..." should be: "...mammal, a swine mammal..."

Signed and Sealed this
Eighth Day of November, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,981,682 B2 | Page 1 of 1 |
| APPLICATION NO. | : 12/927620 | |
| DATED | : July 19, 2011 | |
| INVENTOR(S) | : Kenneth M. Evans | |

It is certified that error appears in the above-identified patent and that said Letters Patent is hereby corrected as shown below:

On the title page item (57), line 6,
Abstract: "…(24) that introduces 0 fluid source…" should be: "(24) that introduces a fluid source…"

col 9, ln 18: "… invention can include an cell…" should be: "…invention can include a cell…"

col 11, ln 58: "…with a flat to slidly accept…" should be: "…with a flat to slidably accept…"

col 16, ln 20:
(Claim 5, line 2) "…element comprises slidly adjust-…" should be: "…element comprises slidably adjust…"

col 16, ln 45:
(Claim 12, line 4) "…a ovine mammal…" should be: "…an ovine mammal…"

col 16, ln 46:
(Claim 12, line 5) "…mammal, swine mammal…" should be: "…mammal, a swine mammal…"

This certificate supersedes the Certificate of Correction issued November 8, 2011.

Signed and Sealed this
Sixth Day of December, 2011

David J. Kappos
*Director of the United States Patent and Trademark Office*

UNITED STATES PATENT AND TRADEMARK OFFICE
CERTIFICATE OF CORRECTION

PATENT NO. : 7,981,682 B2
APPLICATION NO. : 12/927620
DATED : July 19, 2011
INVENTOR(S) : Kenneth M. Evans It is certified that error appears in the above-identified patent and that said Letters Patent is hereby corrected as shown below:

On the Title Page of the Issued Patent, item (62) should read as follows:

"Division of US Patent Application 10/524,793, filed October 20, 2005, now US Patent 7,855,078, which is a National Phase of PCT/US03/25812, filed August 15, 2003, which claims priority to US Application 60/404,279, filed August 15, 2002."

Signed and Sealed this
Eleventh Day of June, 2013

Teresa Stanek Rea
*Acting Director of the United States Patent and Trademark Office*